(12) United States Patent
Maminakis

(10) Patent No.: US 12,119,085 B2
(45) Date of Patent: Oct. 15, 2024

(54) SYSTEM AND METHOD OF MAKING PREDICTIONS OF MATURE CANNABIS PLANTS FROM SEEDLING INFORMATION

(71) Applicant: Cannamatrix Inc., Shrewsbury, MA (US)

(72) Inventor: Emanuel Maminakis, Shrewsbury, MA (US)

(73) Assignee: Cannamatrix Inc., Shrewsbury, MA (US)

( * ) Notice: Subject to any disclaimer, the term of this patent is extended or adjusted under 35 U.S.C. 154(b) by 0 days.

(21) Appl. No.: 18/377,167

(22) Filed: Oct. 5, 2023

(65) Prior Publication Data

US 2024/0105278 A1    Mar. 28, 2024

Related U.S. Application Data

(63) Continuation of application No. 18/222,197, filed on Jul. 14, 2023, now Pat. No. 11,810,645.

(60) Provisional application No. 63/389,114, filed on Jul. 14, 2022.

(51) Int. Cl.
*G16B 20/00* (2019.01)

(52) U.S. Cl.
CPC .................. *G16B 20/00* (2019.02)

(58) Field of Classification Search
CPC ..... G01N 33/4833; G01N 33/49; H01J 49/40; H01J 49/164
USPC .......................... 250/281, 282, 288
See application file for complete search history.

(56) References Cited

U.S. PATENT DOCUMENTS

| | | | |
|---|---|---|---|
| 9,095,554 B2 | 8/2015 | Lewis et al. | |
| 9,529,891 B2 | 12/2016 | Daly et al. | |
| 2004/0049059 A1 | 3/2004 | Mueller | |
| 2022/0076356 A1* | 3/2022 | Cabigon | G06Q 10/0637 |

FOREIGN PATENT DOCUMENTS

| | | | |
|---|---|---|---|
| WO | WO-2017214445 A1 * | 12/2017 | A01H 1/02 |

OTHER PUBLICATIONS

"Cannatype: Cannabis Chemical Profiling", https://groups.ischool.berkeley.edu/CannaType/index.html (accessed Oct. 6, 2022), 2 pages.

* cited by examiner

*Primary Examiner* — Michael Maskell
(74) *Attorney, Agent, or Firm* — GTC Law Group PC & Affiliates

(57) ABSTRACT

Systems and methods of predicting a Cannabis chemotype from genetic data include obtaining a training dataset comprising genetic data for at least one mature Cannabis plant, and corresponding chemotype information for the at least one mature Cannabis plant, generating a chemotype prediction model based on the training dataset, the chemotype prediction model being able to predict the chemotype of a mature Cannabis plant, receiving genetic data for a Cannabis seedling, and predicting, via the chemotype prediction model, the chemotype of the Cannabis seedling upon maturation.

16 Claims, 8 Drawing Sheets

---

OBTAINING A TRAINING DATASET COMPRISING GENETIC DATA AND CORRESPONDING CHEMOTYPE INFORMATION FOR AT LEAST ONE MATURE CANNABIS PLANT 102

↓

GENERATING A CHEMOTYPE PREDICTION MODEL BASED ON THE TRAINING DATASET, THE CHEMOTYPE PREDICTION MODEL BEING ABLE TO PREDICT THE CHEMOTYPE OF A CANNABIS SEEDLING UPON MATURATION 104

Fig. 6

| Identifiers | | Cannabinoid Potency % | | | | Terpene Potency % | | | | | | | | | | | | Raw Genetic Data | | Advanced Statistics | |
|---|---|---|---|---|---|---|---|---|---|---|---|---|---|---|---|---|---|---|---|---|---|
| Plant ID # | Strain Name | THC | CBD | CBG | CBC | B-Caryophyllene | Myrcene | Limonene | Linalool | Eucalyptol | Pinene | Humulene | Geraniol | Camphene | Nerolidol | Isopulegol | Ocimene | Terpinolene | Others... | Row | Row... | Potency Coefficients | Search Engine Tags |
| 10101 0420 | MediHaze | 9.4 | 14.8 | 1.1 | 1 | 0.23 | 1.45 | 0.25 | 0.05 | 0 | 0.1 | 0.08 | 0 | 0.02 | 0.01 | 0 | 0 | 0 | ... | 1 | ... | ... | ... |
| | | | | | | | | | | | | | | | | | | | | A, C, T, G 0/1 | ... | ... | ... |

602 604 608 610 612

SYSTEM AND METHOD OF MAKING PREDICTIONS OF MATURE CANNABIS PLANTS FROM SEEDLING INFORMATION

CLAIM TO PRIORITY

This application is a continuation of U.S. patent application Ser. No. 18/222,197, filed Jul. 14, 2023.

U.S. patent application Ser. No. 18/222,197 claims the benefit of the following provisional patent application: U.S. Provisional Application No. 63/389,114, filed Jul. 14, 2022.

Each of the foregoing patent applications is incorporated herein by reference in their entirety for all purposes.

BACKGROUND

Field

The present disclosure pertains to prediction models of mature plants based on seedling genetics, and the propagation and cultivation of plants, including all Cannabis varieties, in all capacities including a commercial capacity or in a home grower capacity.

Description of the Related Art

Plants, such as Cannabis, with valuable medicinal, chemical, recreational, and utilization profiles may have complex secondary metabolite structuring and corresponding complex gene markers which makes them challenging to reliably propagate and cultivate. Additionally, clonal propagation may result in clonal degradation of valuable properties.

There remains a need for systems and methods to facilitate propagation and cultivation of plants with valuable properties.

SUMMARY

In some aspects, the techniques described herein relate to a computer-implemented method, including: obtaining a training dataset including: genetic data for at least one mature Cannabis plant; and corresponding chemotype information for the at least one mature Cannabis plant, the chemotype including at least one of a cannabinoid profile or a terpene profile; and generating a chemotype prediction model based on the training dataset, the chemotype prediction model being able to predict the chemotype of a Cannabis seedling upon maturation.

In some aspects, the techniques described herein relate to a non-transitory computer-readable medium having stored thereon instructions that, in response to execution, cause a processor to perform operations, the operations, including: obtaining a training dataset including: genetic data for at least one mature Cannabis plant; and corresponding chemotype information for the at least one mature Cannabis plant, the chemotype including at least one of a cannabinoid profile or a terpene profile; and generating a chemotype prediction model based on the training dataset, the chemotype prediction model being able to predict the chemotype of a Cannabis seedling upon maturation.

In some aspects, the techniques described herein relate to a system, including: one or more processors; and one or more computer readable hardware storage devices having stored computer-executable instructions that are executable by the one or more processors to cause the system to at least: obtain a training dataset including: genetic data for at least one mature Cannabis plant; and corresponding chemotype information for the at least one mature Cannabis plant, the chemotype including at least one of a cannabinoid profile or a terpene profile; and generate a chemotype prediction model based on the training dataset, the chemotype prediction model being able to predict the chemotype of a Cannabis seedling upon maturation.

In some aspects, the techniques described herein relate to a computer-implemented method, including: obtaining a chemotype prediction model configured through training to determine a chemotype of a mature Cannabis plant; receiving genetic data for a Cannabis seedling; and predicting, via the chemotype prediction model, the chemotype of the Cannabis seedling upon maturation.

In some aspects, the techniques described herein relate to a non-transitory computer-readable medium having stored thereon instructions that, in response to execution, cause a processor to perform operations, the operations, including: obtaining a chemotype prediction model configured through training to determine a chemotype of a mature Cannabis plant; receiving genetic data for a Cannabis seedling; and predicting, via the chemotype prediction model, the chemotype of the Cannabis seedling upon maturation.

In some aspects, the techniques described herein relate to a system, including: one or more processors; and one or more computer readable hardware storage devices having stored computer-executable instructions that are executable by the one or more processors to cause the system to at least: obtain a chemotype prediction model configured through training to determine a chemotype of a mature Cannabis plant; receive genetic data for a Cannabis seedling; and predict, via the chemotype prediction model, the chemotype of the Cannabis seedling upon maturation.

In some aspects, the techniques described herein relate to a computer-implemented method, including: populating a training dataset with genetic data paired with chemotype information for a plurality of mature Cannabis plants, the chemotype information including at least one of a cannabinoid profile or a terpene profile; training a chemotype prediction model with the training dataset to obtain a trained chemotype prediction model; receiving genetic data for a Cannabis seedling; and predicting, via the trained chemotype prediction model, a chemotype of the Cannabis seedling.

In some aspects, the techniques described herein relate to a non-transitory computer-readable medium having stored thereon instructions that, in response to execution, cause a processor to perform operations, the operations, including: populating a training dataset with genetic data paired with chemotype information for a plurality of mature Cannabis plants, the chemotype information including at least one of a cannabinoid profile or a terpene profile; training a chemotype prediction model with the training dataset to obtain a trained chemotype prediction model; receiving genetic data for a Cannabis seedling; and predicting, via the trained chemotype prediction model, a chemotype of the Cannabis seedling.

In some aspects, the techniques described herein relate to a system, including: one or more processors; and one or more computer readable hardware storage devices having stored computer-executable instructions that are executable by the one or more processors to cause the system to at least: populate a training dataset with genetic data paired with chemotype information for a plurality of mature Cannabis plants, the chemotype information including at least one of a cannabinoid profile or a terpene profile; train a chemotype prediction model with the training dataset to obtain a trained chemotype prediction model; receive genetic data for a Cannabis seedling; and predicting, via the trained chemotype prediction model, a chemotype of the Cannabis seedling.

In some aspects, the techniques described herein relate to a computer-implemented method, including: obtaining a training dataset including: genetic data for at least one mature Cannabis plant; and corresponding chemotype information for the at least one mature Cannabis plant, the chemotype including at least one of a cannabinoid profile or a terpene profile; generating a chemotype prediction model based on the training dataset, the chemotype prediction model being able to predict the chemotype of a mature Cannabis plant; receiving genetic data for a Cannabis seedling; and predicting, via the chemotype prediction model, the chemotype of the Cannabis seedling upon maturation.

In some aspects, the techniques described herein relate to a non-transitory computer-readable medium having stored thereon instructions that, in response to execution, cause a processor to perform operations, the operations, including: obtaining a training dataset including: genetic data for at least one mature Cannabis plant; and corresponding chemotype information for the at least one mature Cannabis plant, the chemotype including at least one of a cannabinoid profile or a terpene profile; generating a chemotype prediction model based on the training dataset, the chemotype prediction model being able to predict the chemotype of a mature Cannabis plant; receiving genetic data for a Cannabis seedling; and predicting, via the chemotype prediction model, the chemotype of the Cannabis seedling upon maturation.

In some aspects, the techniques described herein relate to a system, including: one or more processors; and one or more computer readable hardware storage devices having stored computer-executable instructions that are executable by the one or more processors to cause the system to at least: obtain a training dataset including: genetic data for at least one mature Cannabis plant; and corresponding chemotype information for the at least one mature Cannabis plant, the chemotype including at least one of a cannabinoid profile or a terpene profile; generate a chemotype prediction model based on the training dataset, the chemotype prediction model being able to predict the chemotype of a mature Cannabis plant; receive genetic data for a Cannabis seedling; and predict, via the chemotype prediction model, the chemotype of the Cannabis seedling upon maturation.

In any of the systems, methods, or computer-readable media disclosed herein, the genetic data may include data from at least one of genetic sequencing, genetic fingerprinting, single nucleotide polymorphisms (SNPs), simple sequence repeats (SSRs), amplified fragment length polymorphisms (AFLPs), low-pass sequencing techniques, genotyping-by-sequencing (GBS), restriction fragment length polymorphisms (RFLPs), or random amplified polymorphic DNA (RAPD). In any of the systems, methods, or computer-readable media disclosed herein, the cannabinoid profile and terpene profile may include potency data of at least one of THC, CBD, CBN, or terpenes. In any of the systems, methods, or computer-readable media disclosed herein, the training dataset may include the sex of the mature Cannabis plant. In any of the systems, methods, or computer-readable media disclosed herein, the Cannabis seedling genetic data may be obtained at least one of at most 5 days, at most 10 days, at most 14 days, at most 30 days, or at most 60 days after germination. In any of the systems, methods, or computer-readable media disclosed herein, the Cannabis seedling genetic data may be obtained between 5 days and 60 days after germination. In any of the systems, methods, or computer-readable media disclosed herein, the chemotype is at least one of a cannabinoid profile and a terpene profile.

In some aspects, the techniques described herein relate to a method for displaying information relating to and facilitating Cannabis plant breeding on a graphical user interface, the method including: dynamically displaying a first genetic information in one of a plurality of locations in a user genetic information region, each location in the user genetic information region corresponding to a Cannabis seedling of a user; dynamically displaying a predicted chemotype of the user Cannabis seedling in response to a result of a chemotype prediction model in a predicted chemotype region, the chemotype prediction model trained to predict a chemotype based on training data including chemotype information paired with genetic information for a plurality of mature Cannabis plants; dynamically displaying a stored Cannabis information in one of a plurality of locations in a stored Cannabis information region, each location in the stored Cannabis information region corresponding to a Cannabis variety, wherein the stored Cannabis information includes at least one of a second genetic information, a chemotype, a metadata, or a preference; and displaying at least one of the user genetic information region or predicted chemotype region adjacent to the stored Cannabis information region, wherein the stored Cannabis information moves in the stored Cannabis information region in response to a user query.

These and other systems, methods, objects, features, and advantages of the present disclosure will be apparent to those skilled in the art from the following detailed description of the preferred embodiment and the drawings.

All documents mentioned herein are hereby incorporated in their entirety by reference. References to items in the singular should be understood to include items in the plural, and vice versa, unless explicitly stated otherwise or clear from the text. Grammatical conjunctions are intended to express any and all disjunctive and conjunctive combinations of conjoined clauses, sentences, words, and the like, unless otherwise stated or clear from the context.

BRIEF DESCRIPTION OF THE FIGURES

The disclosure and the following detailed description of certain embodiments thereof may be understood by reference to the following figures:

FIG. 6 depicts a data structure for Cannabis information.

DETAILED DESCRIPTION

Figure 1:
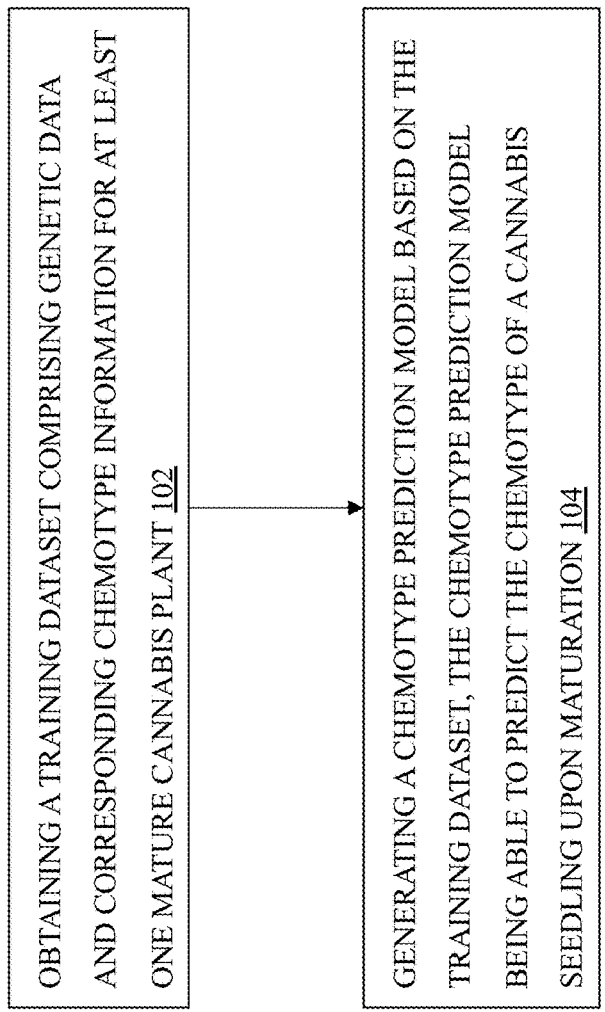
FIG. 1 depicts a flowchart with steps for a training phase of a model.

Throughout this specification, the examples relate primarily to Cannabis varieties but it should be understood that the systems and methods disclosed herein may relate to making prediction models of mature plants of any species based on seedling genetics. Throughout this Specification, the terms grower, cultivator, breeder, user, and customer are used. It should be understood that any of these terms may be used interchangeably to refer to a person, persons, or entity associated with the growth, propagation, cultivation, breeding, study, analysis, management or the like of any Cannabis variety at any stage.

Cannabis is a genus of flowering plants in the family Cannabaceae, which includes three primary species: *Cannabis sativa L., Cannabis indica,* and *Cannabis ruderalis.* Throughout this specification, it should be understood that the term Cannabis includes any of these species, any *Cannabis cultivars,* or any *Cannabis chemovars.*

These plants are native to Central Asia and the Indian subcontinent, but their cultivation has spread worldwide due to their widespread use for medicinal, recreational, and industrial purposes. Cannabis plants are typically dioecious, meaning they have male and female individual organisms, but monoecious varieties also exist. They are known for their characteristic palmately compound leaves with serrated leaflets.

Cannabis plants are highly adaptive and can be grown in a wide variety of climates and soils, which has contributed to their global distribution. For cultivation, they prefer a humid climate and well-drained, rich soils. They are typically grown from seeds, but cloning from cuttings is also common, especially in commercial operations. The plants have a short annual lifecycle, usually flowering in late summer and early fall. A key aspect of Cannabis cultivation is the separation of male and female plants, as female plants produce the buds rich in cannabinoids, the psychoactive compounds, particularly in the absence of male plants.

The cultivation of Cannabis has evolved significantly over the centuries. In modern times, it is often grown indoors under controlled conditions to optimize yield and potency. This involves carefully managing variables such as light exposure, temperature, humidity, and nutrient supply. Different strains of Cannabis have been selectively bred to produce plants with desired traits such as higher THC (tetrahydrocannabinol) or CBD (cannabidiol) content, or specific flavor profiles. Today, the Cannabis industry continues to innovate with more advanced cultivation techniques and genetic modifications to meet the demands of both medicinal and recreational users.

Cannabis has gained significant scientific interest in recent years due to its medical, recreational, industrial and other applications. However, one of the challenges that cultivators face is the unpredictability of Cannabis genetics. Cannabis plants exhibit a wide range of characteristics, including differences in growth rate, yield, cannabinoid profile, or terpene profile, for example, which can make it difficult for cultivators to predict the properties of a given seedling and select the best plants for commercial cultivation.

The seed and/or seedling selection process can only occur at the rate of the life cycle of a Cannabis plant. The life cycle of a Cannabis plant begins with seed propagation, where the seeds germinate and develop into seedlings within 0-14 days. The seedlings then progress into the vegetative stage, lasting 3-16 weeks, characterized by vigorous growth and the development of leaves and branches. Following the vegetative stage, the plant enters the pre-flowering stage for 1-2 weeks, displaying pre-flowers that indicate its sex. The flowering stage, lasting 6-12 weeks, is initiated by adjusting the light cycle and results in the production of female flowers or male pollen. Harvesting can occur within 8-12 weeks from the start of the flowering stage, depending on the desired potency, chemotype/chemical profile (e.g., cannabinoid, terpene, volatile sulfur compounds (VSCs), flavonoids, etc.), characteristics, and/or effects. Alternatively, if seed harvesting is the goal, pollination occurs during the flowering stage, and mature seeds can be collected within 4-6 weeks after pollination. The length of each stage of a Cannabis plant is what makes the seed and/or seedling selection process so important for resource management and crop success.

Traditional methods of seed and/or seedling selection rely on visual inspections and trial-and-error methods, which are time-consuming and can lead to significant losses and/or delays if the wrong plants are selected for cultivation. Traditionally, it takes 60 to 100 days to grow seedlings and to be able to distinguish between drug-type Cannabis plants and fiber-type Cannabis. A seedling that grows into a mature male Cannabis plant has unknown traits to the cultivator until 200-250 days after initial germination. This requires pollination of a subsequent female plant and a second generation to be germinated to determine the properties of a male.

To address this challenge, this disclosure provides methods and systems of using genetic and potency data of at least one of a Cannabis plant seed or Cannabis seedling, to make predictions of the potency and other characteristics of a mature Cannabis plant. It should be understood that seedlings may be at any stage in their lifecycle when sampled for predictive purposes. The systems and methods of the disclosure enable distinguishing plants of various types and possessing various characteristics just days after germination, such as between 5-100 days, or between 5-7 days, or between 6-9 days, or between 8-12 days, or between 10-14 days, or between 10-30 days, or between 5-60 days, including but not limited to, at least 5 days at least 10 days, at least 14 days, at least 30 days, at least 60 days, at most 5 days, at most 10 days, at most 14 days, at most 30 days, or at most 60 days.

There are various methods of obtaining genetic data that can be utilized to characterize and analyze Cannabis varieties, including genetic sequencing, genetic fingerprinting, or a not-yet-known method of obtaining genetic data applied to any portion or whole of a genetic sequence, including the nuclear genome, the mitochondrial genome, or the chloroplast genome. These include single nucleotide polymorphisms (SNPs), which involve single base pair changes in the DNA sequence, and simple sequence repeats (SSRs), which are short repetitive DNA sequences. Amplified fragment length polymorphisms (AFLPs) utilize restriction enzymes and PCR to selectively amplify DNA fragments for comparison. Low-pass sequencing techniques provide partial genomic sequences, while genotyping-by-sequencing (GBS) allows for the discovery and genotyping of numerous SNPs simultaneously. Restriction fragment length polymorphisms (RFLPs) involve the detection of variations in DNA fragment sizes, and random amplified polymorphic DNA (RAPD) utilizes random primers to amplify DNA segments. Other methodologies to obtain genetic information may include one or more of chloroplast DNA sequencing, Low Pass Whole Genome Sequencing (LP-WGS), Polymerase Chain Reaction (PCR), Short Tandem Repeat (STR) analysis, DNA Microarray, Mitochondrial DNA (mtDNA) sequencing, Y-chromosome analysis, Sanger sequencing, Next-generation sequencing (NGS), Illumina sequencing, Ion Torrent sequencing, Pacific Biosciences (PacBio) sequencing, Oxford Nanopore sequencing, pyrosequencing, Massively Parallel Signature Sequencing (MPSS), or third-generation sequencing.

It should be understood that genetic data may be obtained by any known or not-yet-known method. It should be understood that genetic data may encompass a partial DNA sequence, a complete DNA sequence, an indication of mutations, variations, omissions, repetitions, or the like.

Potency data may include information about the levels of various cannabinoids, such as THC (Tetrahydrocannabinol), CBD (Cannabidiol), and CBN (Cannabinol), as well as the levels of terpenes, which are responsible for the plant's aroma and flavor profile. The potency data is obtained through various known and not-yet-known analytical methods, such as HPLC (High-Performance Liquid Chromatography), GC-MS (Gas Chromatography-Mass Spectrometry), and NMR (Nuclear Magnetic Resonance). Throughout this specification, the terms chemotype and chemical profile may be used interchangeably and may refer to a profile of one or more of cannabinoid, terpene, volatile sulfur compounds (VSCs), flavonoids, metabolites, secondary metabolites, or the like. Examples in the Specification typically refer to cannabinoids or terpenes but it should be understood that any chemical characteristic may be used in the system and methods disclosed herein.

Genetic and potency data are important components of Cannabis breeding and cultivation, as they determine the plant's chemical profile, including the levels of cannabinoids and terpenes, which are secondary metabolites of the Cannabis plant, which are responsible for the plant's medicinal and recreational effects. The genetic data includes information about the plant's genetic markers.

In an embodiment, genetic data and potency data for various Cannabis varieties may be correlated or otherwise associated in a database. The database may be structured to enable efficient and accurate prediction of the properties (e.g., cannabinoid and/or terpene profile) of a Cannabis seedling based on genetic similarities with varieties/plants in the database. For example, the database may be structured to be searched by a search engine that uses a series of algorithms to compare the genetic data of the seedling to the data in the database, identifying the most similar varieties and making predictions based on the search engine results. By generating predictions based on genetic data, cultivators can select the best plants for their commercial cultivation, improving the efficiency and profitability of their operations. In some embodiments, prediction algorithms may factor in genetic similarities between the test seedling and varieties in the database, grower/cultivator preferences, sex of the plant, quantitative data (e.g. cannabinoid profile, terpene profile, VSC profile, flavonoid profile), qualitative data (e.g., user experience data), metadata, etc., and users may be able to tailor predictions to their specific needs and preferences. In some embodiments, genetic sequences may be tagged and the search engine may simply look for the presence of one or more similar tags in the database of information. By utilizing a prediction algorithm and search engine function attached to the database, a cannabinoid and terpene profile can be created from a male plant.

In an embodiment, an illustrative and non-limiting example method of an artificial intelligence (AI) model, such as a chemotype prediction model, to learn genetic data that is predictive or correlated with certain chemotypes is depicted. For example, genetic data for mature Cannabis plants may be correlated with levels of THC so that the AI can be trained, or learn, what genetic profiles result in low THC and which ones result in high THC. The model may then be used to predict a THC level for a Cannabis seedling based on its genetic data.

In embodiments, the training dataset may include genetic data and potency data of individual Cannabis plants. The genetic data may include information about the genetic makeup of each variety, such as its DNA sequence or portions thereof, the presence or absence of certain genes or mutations, and the like. The potency data may include information about the cannabinoid and terpene profiles of each variety, which can be used to predict the properties of a seedling based on its genetic makeup. While the primary examples in this specification involve the use of genetic data to predict a chemotype, it should be understood that other characteristics may be predicted based on genetic makeup and an AI model may be trained for such prediction. For example, certain other data may be used to train the model, such as user experience, qualitative data (e.g., taste, smell, or the like), cultivator or breeder preference, metadata, and the like. For example, the model may be trained to predict a particular user-experienced feeling (e.g., a flow state) or a user-experienced taste (e.g., lemony) based on genetic data.

Referring now to FIG. 1, a computer-implemented method may include obtaining a training dataset including genetic data for at least one mature Cannabis plant; and corresponding chemotype information for the at least one mature Cannabis plant 102. The chemotype may include at least one of a cannabinoid profile or a terpene profile. The method may include generating a chemotype prediction model based on the training dataset 104. The chemotype prediction model may be able to predict the chemotype of a Cannabis seedling upon maturation.

The training dataset may be used to train the chemotype prediction model. The trained chemotype prediction model may be applied to genetic data for Cannabis seedlings with unknown chemotypes in order to predict what its chemotype would be upon maturation. The prediction may be based on criteria including one or more of a similarity in a DNA sequence, a % similarity in a portion of a DNA sequence, a presence of a particular DNA sequence/gene, an absence of a particular DNA sequence/gene, a presence or absence of a particular mutation, or any of the genetic data described herein, wherein a user may define the criteria. In some embodiments, the chemotype prediction model may be programmed to predict in accordance with a criteria defined by a user.

For example, a user may first input genetic information for a subject Cannabis seedling and run the chemotype prediction model on the genetic information in order to predict a chemotype. The chemotype prediction model, having been trained on collected data that pairs known genetics with known chemotypes for a plurality of Cannabis plants, can be applied to the input genetic information to predict what the seedling's chemotype would be upon maturation. In some embodiments, the genetic data may be conditioned for improved data storage and use in the user interface. Supervised methods are trained on examples with labels. For example, training data may include a genetic sequence labeled with 'high THC gene' and/or 'low limonene'. The labelled training data are then used to predict these labels on other examples of sequences, whereas unsupervised methods find patterns in data sets without the use of labels. Semi-supervised methods combine these two approaches, leveraging patterns in unlabeled data to improve power in the prediction of labels. In an embodiment, the output of a prediction may be an annotated genetic sequence. In another embodiment, the output of a prediction may be a display of chemotype elements. While this disclosure primarily focuses on supervised methods, it should be understood that any of these training methods may be useful in the systems and methods disclosed herein.

Figure 2:
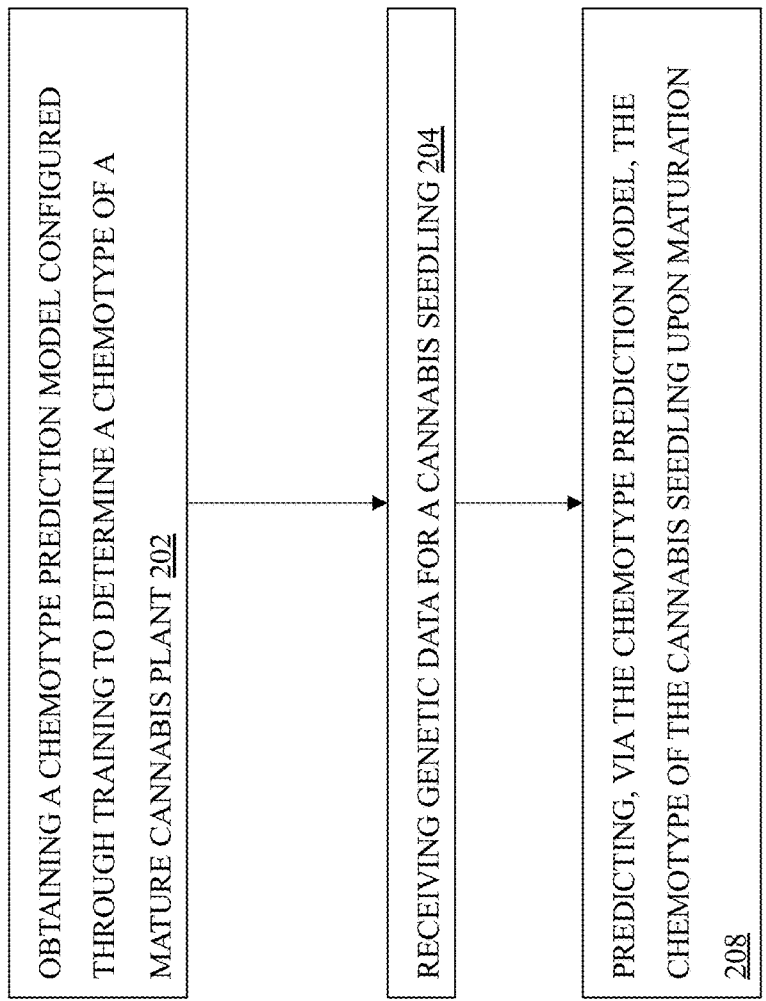
FIG. 2 depicts a flowchart with steps for an inference making phase of a model.

Referring now to FIG. 2, a computer-implemented method may include obtaining a chemotype prediction model configured through training to determine a chemotype of a mature Cannabis plant 202, receiving genetic data for a Cannabis seedling 204, and predicting, via the chemotype prediction model, the chemotype of the Cannabis seedling upon maturation 208.

Figure 3:
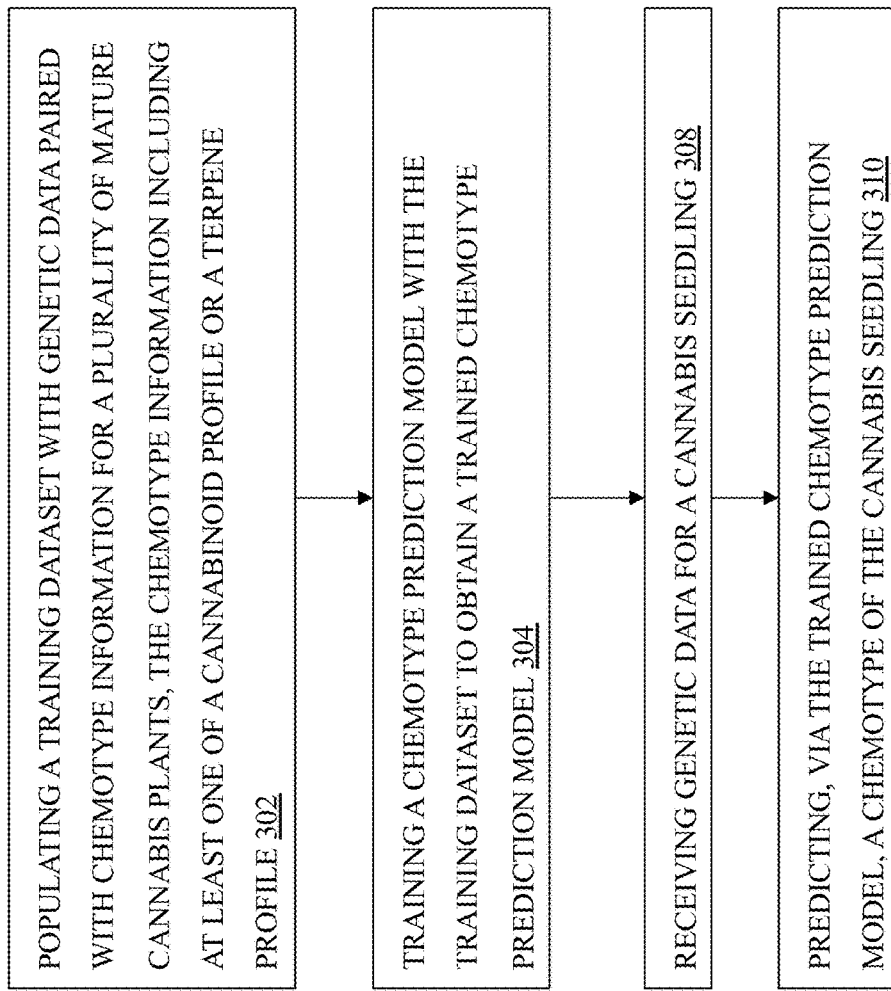
FIG. 3 depicts a flowchart with steps for a training phase and an inference making phase of a model.

Referring to FIG. 3, a computer-implemented method may include populating a training dataset with genetic data paired with chemotype information for a plurality of mature Cannabis plants, the chemotype information including at least one of a cannabinoid profile or a terpene profile 302, training a chemotype prediction model with the training dataset to obtain a trained chemotype prediction model 304, receiving genetic data for a Cannabis seedling 308, and predicting, via the trained chemotype prediction model, a chemotype of the Cannabis seedling 310.

Figure 4:
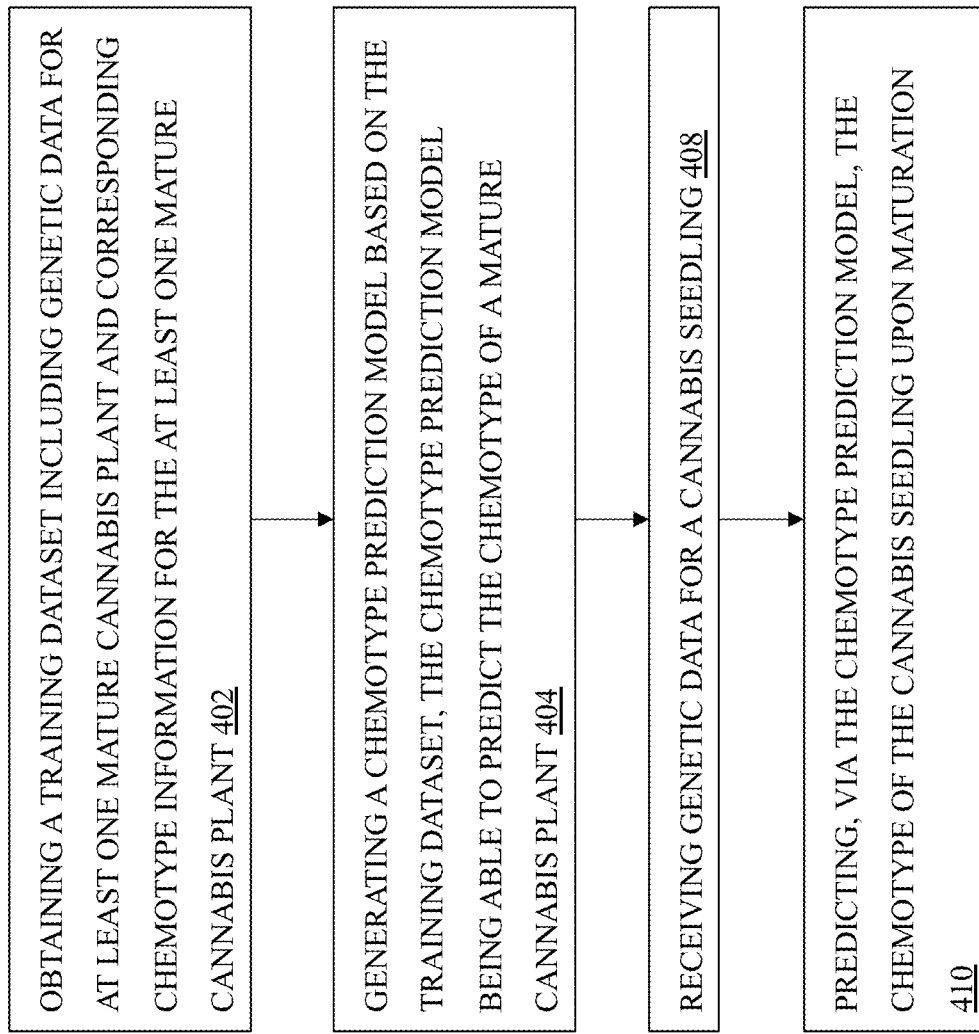
FIG. 4 depicts a flowchart with steps for a training phase and an inference making phase of a model.

Referring to FIG. 4, a computer-implemented method may include obtaining a training dataset including genetic data for at least one mature Cannabis plant and corresponding chemotype information for the at least one mature Cannabis plant, the chemotype including at least one of a cannabinoid profile or a terpene profile 402, generating a chemotype prediction model based on the training dataset, the chemotype prediction model being able to predict the chemotype of a mature Cannabis plant 404, receiving genetic data for a Cannabis seedling 408, and predicting, via the chemotype prediction model, the chemotype of the Cannabis seedling upon maturation 410.

In any of the embodiments disclosed herein, the genetic data may include data from at least one of genetic sequencing, genetic fingerprinting, single nucleotide polymorphisms (SNPs), simple sequence repeats (SSRs), amplified fragment length polymorphisms (AFLPs), low-pass sequencing techniques, genotyping-by-sequencing (GBS), restriction fragment length polymorphisms (RFLPs), or random amplified polymorphic DNA (RAPD).

In any of the embodiments disclosed herein, the cannabinoid profile and terpene profile may include potency data of at least one of THC, CBD, CBN, or terpenes.

In any of the embodiments disclosed herein, the training dataset may include the sex of the mature Cannabis plant.

In any of the embodiments disclosed herein, the Cannabis seedling genetic data may be obtained at least one of at most 5 days, at most 10 days, at most 14 days, at most 30 days, or at most 60 days after germination.

In any of the embodiments disclosed herein, the chemotype is at least one of a cannabinoid profile and a terpene profile.

In an embodiment, a user interface may be used to obtain grower/cultivator preferences, present female Cannabis data (e.g., such as on a cultivator-specific interface or tab), present male Cannabis data (e.g., such as on a breeder-specific interface or tab), or the like. The user interface may enable users to compare genetic information with other users (e.g., cultivators/breeders), such as in a forum, and discover what Cannabis varieties are being cultivated that might be a good match for their male or female plants. In an embodiment, the user interface may enable communication between users, such as through chat, video, audio, or asynchronous messaging, to discuss seed collaborations based on their plant predictions, or other matters. In an embodiment, a social media feature may allow users to communicate with each other and create collaborations.

In embodiments, the user interface may enable access to the chemotype prediction model. A user may apply the chemotype prediction model to genetic information for a seedling to predict a chemotype. Any one of the predicted chemotype, the genetic information, metadata, and user preferences may be used to search a database including collected and stored information about Cannabis plants, Cannabis varieties, and growers/cultivators. The collected information may include the data that was in the training dataset. For example, a user with a Cannabis seedling having a predicted chemotype of low THC may use the user interface to search for a desired mate for their Cannabis seedling along any number of criteria, including genetic sequences, chemotype, metadata, preferences (e.g., a user's own preference of the potential match's preferences), or the like.

Referring to FIG. 6, an entry in the database is shown depicting the database structure. In some embodiments, the database contains identifiers 602, cannabinoid potency percentage 604, terpene potency percentage 608, raw genetic data 610, and advanced statistics 612. The identifiers may be used to organize the data by number and by name and may include plant ID, which may be a unique number for that specific organism, and a strain name used for customer convenience. "Strain" is a term used by Cannabis cultivators, and can be interchangeably used with organism, variety, cultivar, etc. The cannabinoid potency percentage 604 may be data derived from Cannabis potency providers. Most legal Cannabis states/regions have licensed potency labs to provide standardization of the potency metrics for cannabinoids. This may include THC, CBD, CBG, CBC, or any phytocannabinoid that naturally occurs in Cannabis. These potency providers may also test for terpene potency percentage 608. Terpenes are natural chemicals that occur in many different plant varieties. Terpenes include, but are not limited to: B-Caryophyllene, Myrcene, Limonene, Linalool, Eucalyptol, Pinene, Humulene, Geraniol, Camphene, Nerolidol, Isopulegol, Ocimene, Terpinene, Terpinolene, and more. There are over 400 known terpenes. Most licensed potency labs in the US have the capability to test for terpenes as well as cannabinoids. Raw genetic data 610 may be in the form of sequencing, genetic markers or fingerprints, or any other method of obtaining numerical data from the DNA of a given organism. This section can be very long since it can cover the entire length of a genomic sequence, which is indicated with a 'Row . . . " column. Each individual column from the genetic data will either contain A, C, T, or G based on the base pairs of the sequence, a binary system indicating the presence or absence of a genetic marker with a 0 or 1, a specific sequence, or the like. The advanced statistics 612 section may include infinite rows of search engine and coefficient based data. Potency coefficients may be based on formulaic results for both Cannabinoid and terpene potency data. Each individual cannabinoid and terpene can be given a coefficient in its own column. A search engine may be used to assign tags based on the Raw genetic data 610. These tags also have infinite columns and they help the search engine find genetic profiles in the database that are similar. A final plant prediction can be derived from the advanced statistics.

Figure 5:
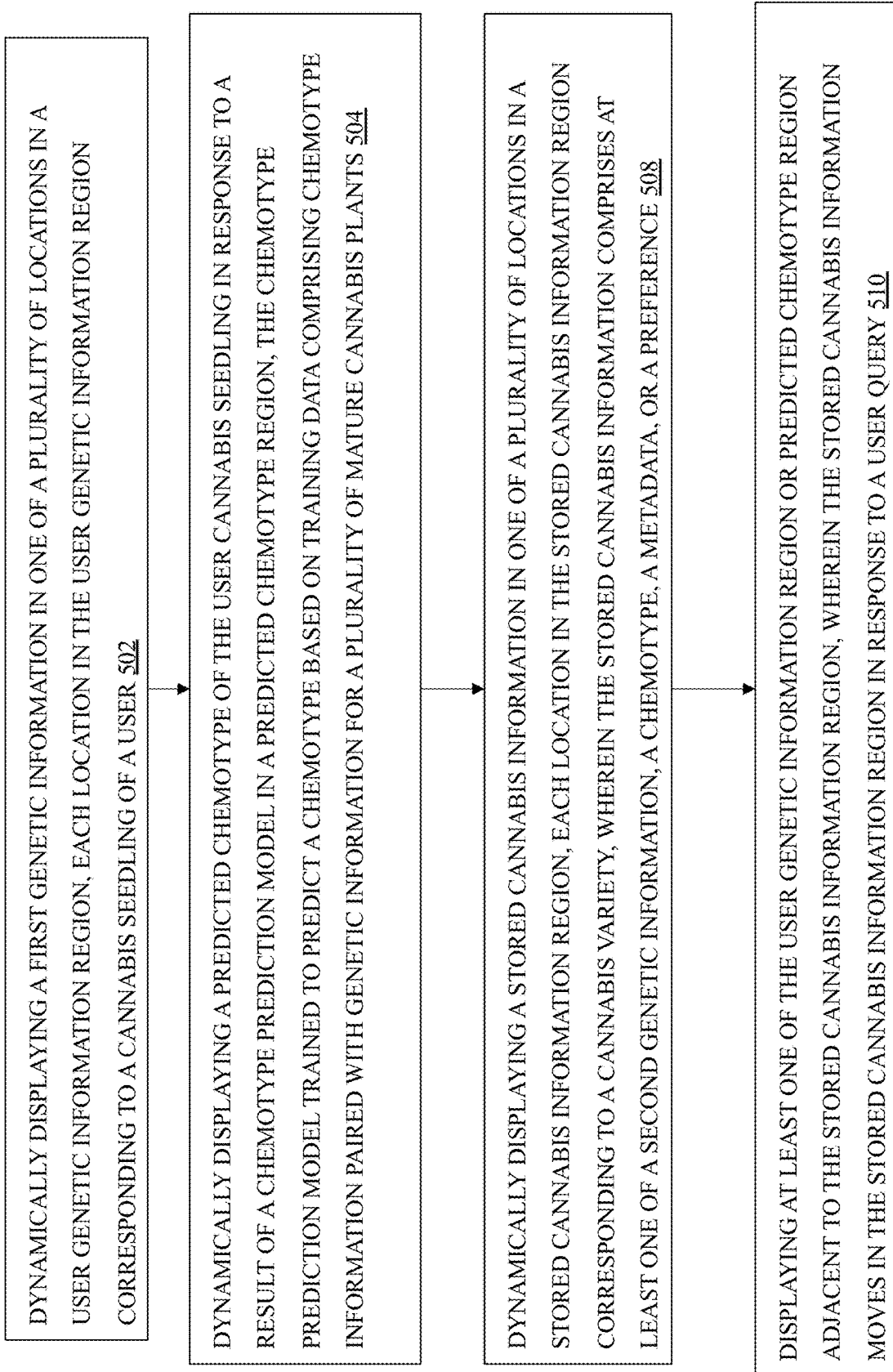
FIG. 5 depicts steps for implementing a user interface.

Referring to FIG. 5, a method for displaying information relating to and facilitating Cannabis plant breeding on a graphical user interface may include dynamically displaying a first genetic information in one of a plurality of locations in a user genetic information region, each location in the user genetic information region corresponding to a Cannabis seedling of a user 502, dynamically displaying a predicted chemotype of the user Cannabis seedling in response to a result of a chemotype prediction model in a predicted chemotype region, the chemotype prediction model trained to predict a chemotype based on training data comprising chemotype information paired with genetic information for a plurality of mature Cannabis plants 504, dynamically displaying a stored Cannabis information in one of a plurality of locations in a stored Cannabis information region, each location in the stored Cannabis information region corresponding to a Cannabis variety, wherein the stored Cannabis information comprises at least one of a second genetic information, a chemotype, a metadata, or a preference 508, and displaying at least one of the user genetic information region or predicted chemotype region adjacent to the stored Cannabis information region, wherein the stored Cannabis information moves in the stored Cannabis information region in response to a user query 510. The user query may include at least one of a genetic criteria, a chemotype criteria, a metadata criteria, or a user preference. The method may include facilitating communication between the user and a second user, the second user associated with at least one result from the user query.

Figure 7:
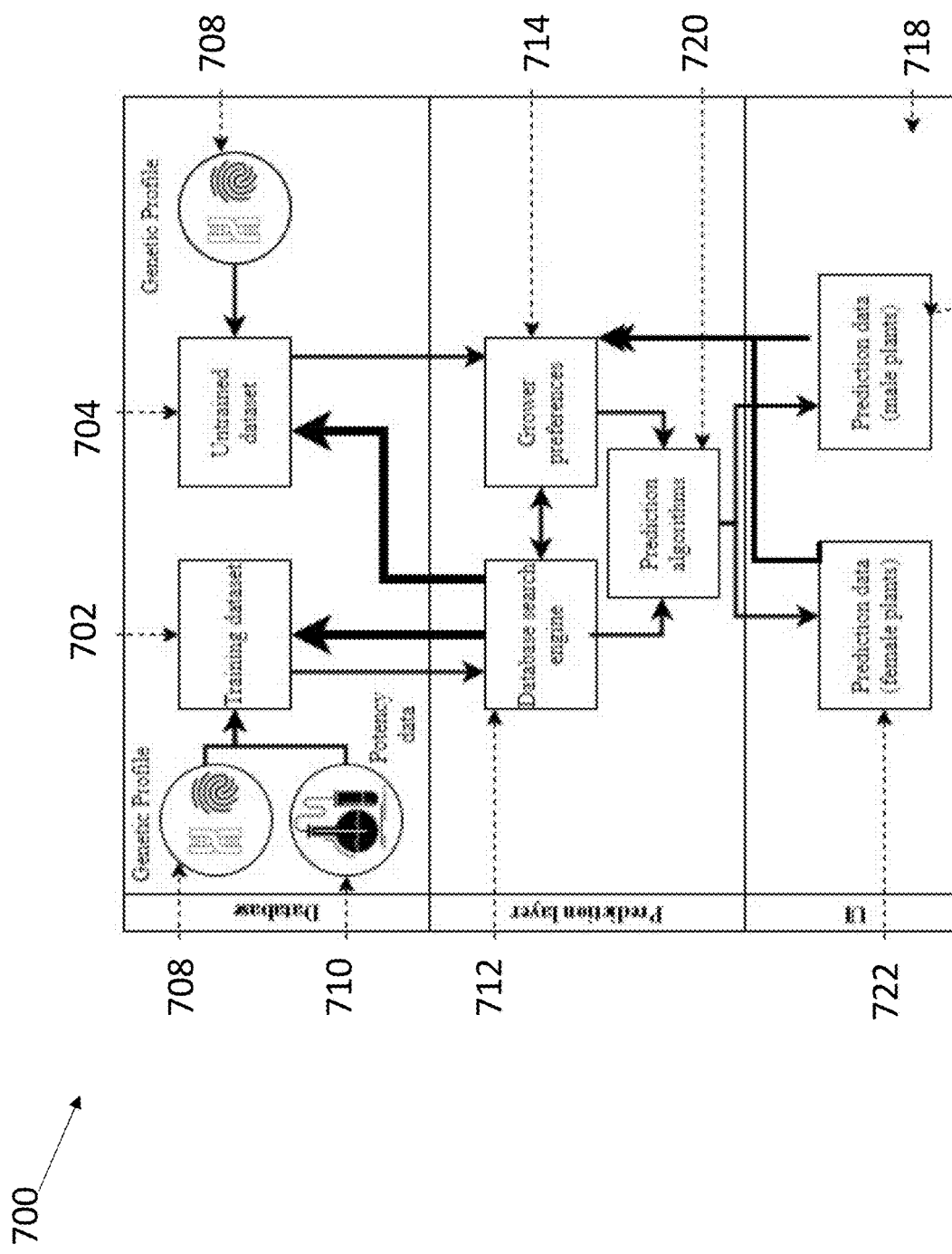
FIG. 7 depicts a system of making predictions of Cannabis seedling chemotype.

Referring now to FIG. 7, an example of a system 700 of the disclosure is depicted. The database layer consists of the training dataset 702 and customer, or untrained, dataset 704. The training dataset is a collection of specific varieties that assist in the prediction of customer data. The training dataset contains genetic data 708 and potency data 710. The customer dataset is a collection of all genetic data that is unpaired with cannabinoid and terpene data. The customer genetic data may be processed through the search engine 712 or an artificial intelligence model to find the most similar varieties in the training dataset. The grower preferences 714 may be sourced by the interface 718 and may be factored into the prediction algorithms 720. The prediction algorithms may be presented to the customer on their web portal interface 718. A cultivator interface 722 may present female Cannabis data, and a breeder interface 724 may be to present male Cannabis data. The customer can compare genetic information with other cultivators in a breeder forum of the interface and discover what Cannabis varieties are being cultivated that might be a good match for their male or female plants. They can connect to other growers through a chat feature and discuss seed collaborations based on their plant predictions.

Figure 8:
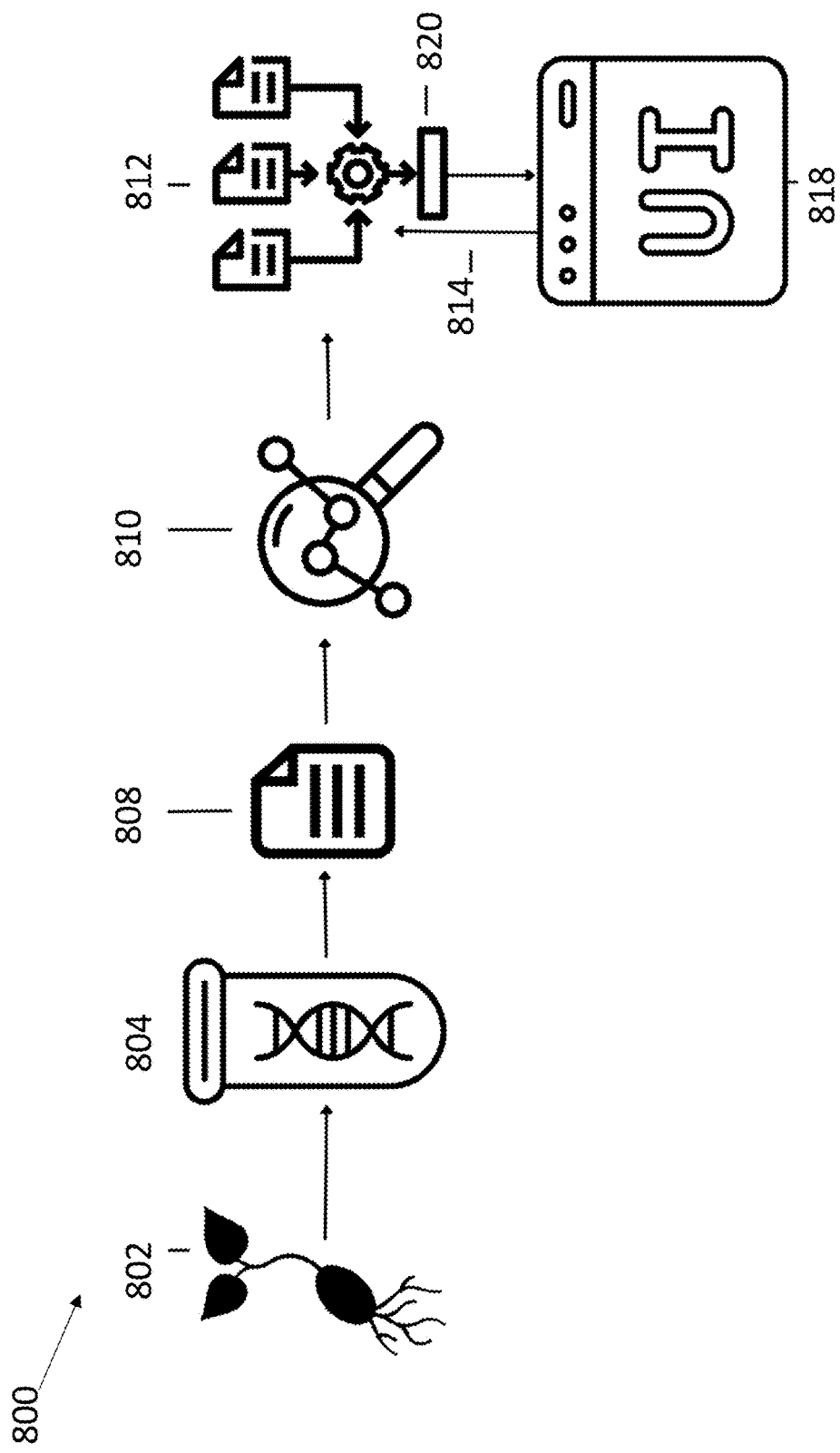
FIG. 8 depicts a process flow of the system of FIG. 7.

Referring now to FIG. 8, a process flow 800 is depicted. The process starts with the germination of Cannabis seeds 802. The genetic data of the seedlings are then collected 804 and entered into a dataset 808. The dataset is processed through the search engine 810 or an artificial intelligence model is applied to the data to find the most similar varieties in a Training dataset 812. The grower preferences may be sourced 814 by the interface 818 and factored into the prediction algorithms 820. The prediction algorithms may generate recommendations for seed selections, which are presented to the customer on their web portal interface 818. The customer can then select their preferred seed and begin the flowering stage.

As described herein, machine learning models may be trained using supervised learning or unsupervised learning. In supervised learning, a model is generated using a set of labeled examples, where each example has corresponding target label(s). In unsupervised learning, the model is generated using unlabeled examples. The collection of examples constructs a dataset, usually referred to as a training dataset. During training, a model is generated using this training data to learn the relationship between examples in the dataset. The training process may include various phases such as: data collection, preprocessing, feature extraction, model training, model evaluation, and model fine-tuning. The data collection phase may include collecting a representative dataset, typically from multiple users, that covers the range of possible scenarios and positions. The preprocessing phase may include cleaning and preparing the examples in the dataset and may include filtering, normalization, and segmentation. The feature extraction phase may include extracting relevant features from examples to capture relevant information for the task. The model training phase may include training a machine learning model on the preprocessed and feature-extracted data. Models may include support vector machines (SVMs), artificial neural networks (ANNs), decision trees, and the like for supervised learning, or autoencoders, Hopfield, restricted Boltzmann machine (RBM), deep belief, Generative Adversarial Networks (GAN), or other networks, or clustering for unsupervised learning. The model evaluation phase may include evaluating the performance of the trained model on a separate validation dataset to ensure that it generalizes well to new and unseen examples. The model fine-tuning may include refining a model by adjusting its parameters, changing the features used, or using a different machine-learning algorithm, based on the results of the evaluation. The process may be iterated until the performance of the model on the validation dataset is satisfactory and the trained model can then be used to make predictions.

In embodiments, trained models may be periodically fine-tuned for specific user groups, applications, and/or tasks. Fine-tuning of an existing model may improve the performance of the model for an application while avoiding completely retraining the model for the application.

In embodiments, fine-tuning a machine learning model may involve adjusting its hyperparameters or architecture to improve its performance for a particular user group or application. The process of fine-tuning may be performed after initial training and evaluation of the model, and it can involve one or more hyperparameter tuning and architectural methods.

Hyperparameter tuning includes adjusting the values of the model's hyperparameters, such as learning rate, regularization strength, or the number of hidden units. This can be done using methods such as grid search, random search, or Bayesian optimization. Architecture modification may include modifying the structure of the model, such as adding or removing layers, changing the activation functions, or altering the connections between neurons, to improve its performance.

Online training of machine learning models includes a process of updating the model as new examples become available, allowing it to adapt to changes in the data distribution over time. In online training, the model is trained incrementally as new data becomes available, allowing it to adapt to changes in the data distribution over time. Online training can also be useful for user groups that have changing usage habits of the stimulation device, allowing the models to be updated in almost real-time.

In embodiments, online training may include adaptive filtering. In adaptive filtering, a machine learning model is trained online to learn the underlying structure of the new examples and remove noise or artifacts from the examples.

The methods and systems described herein may be deployed in part or in whole through a machine having a computer, computing device, processor, circuit, and/or server that executes computer readable instructions, program codes, instructions, and/or includes hardware configured to functionally execute one or more operations of the methods and systems disclosed herein. The terms computer, computing device, processor, circuit, and/or server, as utilized herein, should be understood broadly.

Any one or more of the terms computer, computing device, processor, circuit, and/or server include a computer of any type, capable to access instructions stored in communication thereto such as upon a non-transient computer readable medium, whereupon the computer performs operations of systems or methods described herein upon executing the instructions. In certain embodiments, such instructions themselves comprise a computer, computing device, processor, circuit, and/or server. Additionally or alternatively, a computer, computing device, processor, circuit, and/or server may be a separate hardware device, one or more computing resources distributed across hardware devices, and/or may include such aspects as logical circuits, embedded circuits, sensors, actuators, input and/or output devices, network and/or communication resources, memory resources of any type, processing resources of any type, and/or hardware devices configured to be responsive to determined conditions to functionally execute one or more operations of systems and methods herein.

Network and/or communication resources include, without limitation, local area network, wide area network, wireless, interne, or any other known communication resources and protocols. Example and non-limiting hardware, computers, computing devices, processors, circuits, and/or servers include, without limitation, a general purpose computer, a server, an embedded computer, a mobile device, a virtual machine, and/or an emulated version of one or more of these. Example and non-limiting hardware, computers, computing devices, processors, circuits, and/or servers may be physical, logical, or virtual. A computer, computing device, processor, circuit, and/or server may be: a distributed resource included as an aspect of several devices; and/or included as an interoperable set of resources to perform described functions of the computer, computing device, processor, circuit, and/or server, such that the distributed resources function together to perform the operations of the computer, computing device, processor, circuit, and/or server. In certain embodiments, each computer, computing device, processor, circuit, and/or server may be on separate hardware, and/or one or more hardware devices may include aspects of more than one computer, computing device, processor, circuit, and/or server, for example as separately executable instructions stored on the hardware device, and/ or as logically partitioned aspects of a set of executable instructions, with some aspects of the hardware device comprising a part of a first computer, computing device, processor, circuit, and/or server, and some aspects of the hardware device comprising a part of a second computer, computing device, processor, circuit, and/or server.

A computer, computing device, processor, circuit, and/or server may be part of a server, client, network infrastructure, mobile computing platform, stationary computing platform, or other computing platform. A processor may be any kind of computational or processing device capable of executing program instructions, codes, binary instructions and the like. The processor may be or include a signal processor, digital processor, embedded processor, microprocessor or any variant such as a co-processor (math co-processor, graphic co-processor, communication co-processor and the like) and the like that may directly or indirectly facilitate execution of program code or program instructions stored thereon. In addition, the processor may enable execution of multiple programs, threads, and codes. The threads may be executed simultaneously to enhance the performance of the processor and to facilitate simultaneous operations of the application. By way of implementation, methods, program codes, program instructions and the like described herein may be implemented in one or more threads. The thread may spawn other threads that may have assigned priorities associated with them; the processor may execute these threads based on priority or any other order based on instructions provided in the program code. The processor may include memory that stores methods, codes, instructions and programs as described herein and elsewhere. The processor may access a storage medium through an interface that may store methods, codes, and instructions as described herein and elsewhere. The storage medium associated with the processor for storing methods, programs, codes, program instructions or other type of instructions capable of being executed by the computing or processing device may include but may not be limited to one or more of a CD-ROM, DVD, memory, hard disk, flash drive, RAM, ROM, cache and the like.

A processor may include one or more cores that may enhance speed and performance of a multiprocessor. In embodiments, the process may be a dual core processor, quad core processors, other chip-level multiprocessor and the like that combine two or more independent cores (called a die).

The methods and systems described herein may be deployed in part or in whole through a machine that executes computer readable instructions on a server, client, firewall, gateway, hub, router, or other such computer and/or networking hardware. The computer readable instructions may be associated with a server that may include a file server, print server, domain server, interne server, intranet server and other variants such as secondary server, host server, distributed server and the like. The server may include one or more of memories, processors, computer readable transitory and/or non-transitory media, storage media, ports (physical and virtual), communication devices, and interfaces capable of accessing other servers, clients, machines, and devices through a wired or a wireless medium, and the like. The methods, programs, or codes as described herein and elsewhere may be executed by the server. In addition, other devices required for execution of methods as described in this application may be considered as a part of the infrastructure associated with the server.

The server may provide an interface to other devices including, without limitation, clients, other servers, printers, database servers, print servers, file servers, communication servers, distributed servers, and the like. Additionally, this coupling and/or connection may facilitate remote execution of instructions across the network. The networking of some or all of these devices may facilitate parallel processing of program code, instructions, and/or programs at one or more locations without deviating from the scope of the disclosure. In addition, all the devices attached to the server through an interface may include at least one storage medium capable of storing methods, program code, instructions, and/or programs. A central repository may provide program instructions to be executed on different devices. In this implementation, the remote repository may act as a storage medium for methods, program code, instructions, and/or programs.

The methods, program code, instructions, and/or programs may be associated with a client that may include a file client, print client, domain client, internet client, intranet client and other variants such as secondary client, host client, distributed client and the like. The client may include one or more of memories, processors, computer readable transitory and/or non-transitory media, storage media, ports (physical and virtual), communication devices, and interfaces capable of accessing other clients, servers, machines, and devices through a wired or a wireless medium, and the like. The methods, program code, instructions, and/or programs as described herein and elsewhere may be executed by the client. In addition, other devices utilized for execution of methods as described in this application may be considered as a part of the infrastructure associated with the client.

The client may provide an interface to other devices including, without limitation, servers, other clients, printers, database servers, print servers, file servers, communication servers, distributed servers, and the like. Additionally, this coupling and/or connection may facilitate remote execution of methods, program code, instructions, and/or programs across the network. The networking of some or all of these devices may facilitate parallel processing of methods, program code, instructions, and/or programs at one or more locations without deviating from the scope of the disclosure. In addition, all the devices attached to the client through an interface may include at least one storage medium capable of storing methods, program code, instructions, and/or programs. A central repository may provide program instructions to be executed on different devices. In this implementation, the remote repository may act as a storage medium for methods, program code, instructions, and/or programs.

The methods and systems described herein may be deployed in part or in whole through network infrastructures. The network infrastructure may include elements such as computing devices, servers, routers, hubs, firewalls, clients, personal computers, communication devices, routing devices and other active and passive devices, modules, and/or components as known in the art. The computing and/or non-computing device(s) associated with the network infrastructure may include, apart from other components, a storage medium such as flash memory, buffer, stack, RAM, ROM and the like. The methods, program code, instructions, and/or programs described herein and elsewhere may be executed by one or more of the network infrastructural elements.

The methods, program code, instructions, and/or programs described herein and elsewhere may be implemented on a cellular network having multiple cells. The cellular network may either be frequency division multiple access (FDMA) network or code division multiple access (CDMA) network. The cellular network may include mobile devices, cell sites, base stations, repeaters, antennas, towers, and the like.

The methods, program code, instructions, and/or programs described herein and elsewhere may be implemented on or through mobile devices. The mobile devices may include navigation devices, cell phones, mobile phones, mobile personal digital assistants, laptops, palmtops, netbooks, pagers, electronic books readers, music players, and the like. These mobile devices may include, apart from other components, a storage medium such as a flash memory, buffer, RAM, ROM and one or more computing devices. The computing devices associated with mobile devices may be enabled to execute methods, program code, instructions, and/or programs stored thereon. Alternatively, the mobile devices may be configured to execute instructions in collaboration with other devices. The mobile devices may communicate with base stations interfaced with servers and configured to execute methods, program code, instructions, and/or programs. The mobile devices may communicate on a peer to peer network, mesh network, or other communications network. The methods, program code, instructions, and/or programs may be stored on the storage medium associated with the server and executed by a computing device embedded within the server. The base station may include a computing device and a storage medium. The storage device may store methods, program code, instructions, and/or programs executed by the computing devices associated with the base station.

The methods, program code, instructions, and/or programs may be stored and/or accessed on machine readable transitory and/or non-transitory media that may include: computer components, devices, and recording media that retain digital data used for computing for some interval of time; semiconductor storage known as random access memory (RAM); mass storage typically for more permanent storage, such as optical discs, forms of magnetic storage like hard disks, tapes, drums, cards and other types; processor registers, cache memory, volatile memory, non-volatile memory; optical storage such as CD, DVD; removable media such as flash memory (e.g., USB sticks or keys), floppy disks, magnetic tape, paper tape, punch cards, stand-alone RAM disks, Zip drives, removable mass storage, off-line, and the like; other computer memory such as dynamic memory, static memory, read/write storage, mutable storage, read only, random access, sequential access, location addressable, file addressable, content addressable, network attached storage, storage area network, bar codes, magnetic ink, and the like.

Certain operations described herein include interpreting, receiving, and/or determining one or more values, parameters, inputs, data, or other information. Operations including interpreting, receiving, and/or determining any value parameter, input, data, and/or other information include, without limitation: receiving data via a user input; receiving data over a network of any type; reading a data value from a memory location in communication with the receiving device; utilizing a default value as a received data value; estimating, calculating, or deriving a data value based on other information available to the receiving device; and/or updating any of these in response to a later received data value. In certain embodiments, a data value may be received by a first operation, and later updated by a second operation, as part of the receiving a data value. For example, when communications are down, intermittent, or interrupted, a first operation to interpret, receive, and/or determine a data value may be performed, and when communications are restored an updated operation to interpret, receive, and/or determine the data value may be performed.

Certain logical groupings of operations herein, for example methods or procedures of the current disclosure, are provided to illustrate aspects of the present disclosure. Operations described herein are schematically described and/or depicted, and operations may be combined, divided, re-ordered, added, or removed in a manner consistent with the disclosure herein. It is understood that the context of an operational description may require an ordering for one or more operations, and/or an order for one or more operations may be explicitly disclosed, but the order of operations should be understood broadly, where any equivalent grouping of operations to provide an equivalent outcome of operations is specifically contemplated herein. For example, if a value is used in one operational step, the determining of the value may be required before that operational step in certain contexts (e.g. where the time delay of data for an operation to achieve a certain effect is important), but may not be required before that operation step in other contexts (e.g. where usage of the value from a previous execution cycle of the operations would be sufficient for those purposes). Accordingly, in certain embodiments an order of operations and grouping of operations as described is explicitly contemplated herein, and in certain embodiments re-ordering, subdivision, and/or different grouping of operations is explicitly contemplated herein.

The methods and systems described herein may transform physical and/or or intangible items from one state to another.

The methods and systems described herein may also transform data representing physical and/or intangible items from one state to another.

The elements described and depicted herein, including in flow charts, block diagrams, and/or operational descriptions, depict and/or describe specific example arrangements of elements for purposes of illustration. However, the depicted and/or described elements, the functions thereof, and/or arrangements of these, may be implemented on machines, such as through computer executable transitory and/or non-transitory media having a processor capable of executing program instructions stored thereon, and/or as logical circuits or hardware arrangements. Example arrangements of programming instructions include at least: monolithic structure of instructions; standalone modules of instructions for elements or portions thereof; and/or as modules of instructions that employ external routines, code, services, and so forth; and/or any combination of these, and all such implementations are contemplated to be within the scope of embodiments of the present disclosure Examples of such machines include, without limitation, personal digital assistants, laptops, personal computers, mobile phones, other handheld computing devices, medical equipment, wired or wireless communication devices, transducers, chips, calculators, satellites, tablet PCs, electronic books, gadgets, electronic devices, devices having artificial intelligence, computing devices, networking equipment, servers, routers and the like. Furthermore, the elements described and/or depicted herein, and/or any other logical components, may be implemented on a machine capable of executing program instructions. Thus, while the foregoing flow charts, block diagrams, and/or operational descriptions set forth functional aspects of the disclosed systems, any arrangement of program instructions implementing these functional aspects are contemplated herein. Similarly, it will be appreciated that the various steps identified and described above may be varied, and that the order of steps may be adapted to particular applications of the techniques disclosed herein. Additionally, any steps or operations may be divided and/or combined in any manner providing similar functionality to the described operations. All such variations and modifications are contemplated in the present disclosure. The methods and/or processes described above, and steps thereof, may be implemented in hardware, program code, instructions, and/or programs or any combination of hardware and methods, program code, instructions, and/or programs suitable for a particular application. Example hardware includes a dedicated computing device or specific computing device, a particular aspect or component of a specific computing device, and/or an arrangement of hardware components and/or logical circuits to perform one or more of the operations of a method and/or system. The processes may be implemented in one or more microprocessors, microcontrollers, embedded microcontrollers, programmable digital signal processors or other programmable device, along with internal and/or external memory. The processes may also, or instead, be embodied in an application specific integrated circuit, a programmable gate array, programmable array logic, or any other device or combination of devices that may be configured to process electronic signals. It will further be appreciated that one or more of the processes may be realized as a computer executable code capable of being executed on a machine readable medium.

The computer executable code may be created using a structured programming language such as C, an object oriented programming language such as C++, or any other high-level or low-level programming language (including assembly languages, hardware description languages, and database programming languages and technologies) that may be stored, compiled or interpreted to run on one of the above devices, as well as heterogeneous combinations of processors, processor architectures, or combinations of different hardware and computer readable instructions, or any other machine capable of executing program instructions.

Thus, in one aspect, each method described above and combinations thereof may be embodied in computer executable code that, when executing on one or more computing devices, performs the steps thereof. In another aspect, the methods may be embodied in systems that perform the steps thereof, and may be distributed across devices in a number of ways, or all of the functionality may be integrated into a dedicated, standalone device or other hardware. In another aspect, the means for performing the steps associated with the processes described above may include any of the hardware and/or computer-readable instructions described above. All such permutations and combinations are contemplated in embodiments of the present disclosure.

While the disclosure has been disclosed in connection with the preferred embodiments shown and described in detail, various modifications and improvements thereon will become readily apparent to those skilled in the art. Accordingly, the spirit and scope of the present disclosure is not to be limited by the foregoing examples, but is to be understood in the broadest sense allowable by law.

What is claimed is:

1. A computer-implemented method for displaying information relating to and facilitating Cannabis plant breeding on a graphical user interface, comprising;
    dynamically displaying a first genetic information in one of a plurality of locations in a user genetic information region, each location in the user genetic information region corresponding to a Cannabis seedling of a user;
    dynamically displaying a predicted chemotype of the user Cannabis seedling in response to a result of a chemotype prediction model in a predicted chemotype region;
    dynamically displaying a stored Cannabis information in one of a plurality of locations in a stored Cannabis information region, each location in the stored Cannabis information region corresponding to a Cannabis variety; and
    displaying at least one of the user genetic information region or predicted chemotype region adjacent to the stored Cannabis information region.

2. The computer-implemented method of claim 1, wherein the genetic information includes data from at least one of genetic sequencing, genetic fingerprinting, single nucleotide polymorphisms (SNPs), simple sequence repeats (SSRs), amplified fragment length polymorphisms (AFLPs), low-pass sequencing techniques, genotyping-by-sequencing (GBS), restriction fragment length polymorphisms (RFLPs), or random amplified polymorphic DNA (RAPD).

3. The computer-implemented method of claim 1, wherein the chemotype information includes at least one of a cannabinoid profile or a terpene profile.

4. The computer-implemented method of claim 3, wherein the cannabinoid profile and terpene profile includes potency data of at least one of THC, CBD, CBN, or terpenes.

5. The computer-implemented method of claim 1, wherein the chemotype prediction model is trained to predict a chemotype based on training data.

6. The computer-implemented method of claim 1, wherein the first genetic information is obtained between 5 days and 60 days after germination.

7. The computer-implemented method of claim 1, wherein the stored Cannabis information comprises at least one of a second genetic information, a chemotype, a metadata, a user experience, a qualitative data, or a preference.

8. The computer-implemented method of claim 7, wherein the user experience is at least one of a feeling, a taste, or a smell.

9. The computer-implemented method of claim 5, wherein the training data includes a sex of a mature Cannabis plant.

10. The computer-implemented method of claim 5, wherein the training data comprises chemotype information and genetic information.

11. The computer-implemented method of claim 10, wherein the chemotype information is paired with the genetic information for a plurality of mature Cannabis plants.

12. The computer-implemented method of claim 1, wherein the stored Cannabis information moves in the stored Cannabis information region in response to a user query.

13. The computer-implemented method of claim 1, wherein a prediction of the chemotype prediction model is based on at least one of a percent similarity in a DNA sequence, a percent similarity in a portion of a DNA sequence, a presence of a particular DNA sequence/gene, an absence of a particular DNA sequence/gene, or a presence or absence of a particular mutation.

14. The computer-implemented method of claim 12, wherein the user query comprises at least one of a genetic criteria, a chemotype criteria, a metadata criteria, a user experience, a qualitative data, or a user preference.

15. The computer-implemented method of claim 14, further comprising, facilitating communication between the user and a second user, the second user associated with at least one result from the user query.

16. The computer-implemented method of claim 14, wherein the user experience is at least one of a feeling, a taste, or a smell.

* * * * *